United States Patent
Florent et al.

(10) Patent No.: US 10,019,800 B2
(45) Date of Patent: Jul. 10, 2018

(54) DEPLOYMENT MODELLING

(71) Applicant: KONINKLIJKE PHILIPS N.V., Eindhoven (NL)

(72) Inventors: Raoul Florent, Suresnes (FR); Odile Bonnefous, Suresnes (FR); Hernan Guillermo Morales Varela, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 54 days.

(21) Appl. No.: 15/109,458

(22) PCT Filed: Dec. 23, 2014

(86) PCT No.: PCT/EP2014/079101
§ 371 (c)(1),
(2) Date: Jul. 1, 2016

(87) PCT Pub. No.: WO2015/101545
PCT Pub. Date: Jul. 9, 2015

(65) Prior Publication Data
US 2016/0335757 A1 Nov. 17, 2016

(30) Foreign Application Priority Data
Jan. 6, 2014 (EP) .................................. 14305009

(51) Int. Cl.
*G06K 9/00* (2006.01)
*G06T 7/00* (2017.01)
(Continued)

(52) U.S. Cl.
CPC ........ *G06T 7/004* (2013.01); *A61B 17/12031* (2013.01); *A61B 17/12113* (2013.01);
(Continued)

(58) Field of Classification Search
None
See application file for complete search history.

(56) References Cited

U.S. PATENT DOCUMENTS 7,840,393 B1 * 11/2010 Whirley ................... G06G 7/48
703/11
8,095,382 B2 * 1/2012 Boyden .............. A61B 5/02007
705/2
(Continued)

FOREIGN PATENT DOCUMENTS

WO 2011121516 A2 10/2011

OTHER PUBLICATIONS

Larrabide, Ignacio et al "Fast Virtual Stenting with Deformable Meshes: Application to Intracranial Aneurysms", Medical Image Computing and Computer-Assisted Intervention (MICCAI), vol. 1, pp. 790-797, 2008.
(Continued)

*Primary Examiner* — Hadi Akhavannik

(57) ABSTRACT

The success of the positioning of devices for deployment inside an aneurysm, for example, is reliant on processes, which take place within an intervention procedure. For example, the position, orientation, or trajectory of the intervention device can affect the final position of a device for deployment deployed on the intervention device. Therefore, it is useful to predict the deployment position of a device for deployment based on a current localization of only the intervention device within an object of interest.

15 Claims, 5 Drawing Sheets

(51) Int. Cl.
*A61B 17/12* (2006.01)
*G06T 7/70* (2017.01)
*A61B 34/10* (2016.01)
*A61B 34/20* (2016.01)
*A61B 34/00* (2016.01)
*A61B 90/00* (2016.01)

(52) U.S. Cl.
CPC ........ *A61B 17/12172* (2013.01); *A61B 34/10* (2016.02); *A61B 90/361* (2016.02); *G06T 7/70* (2017.01); *A61B 2034/104* (2016.02); *A61B 2034/107* (2016.02); *A61B 2034/2074* (2016.02); *A61B 2034/254* (2016.02); *A61B 2090/364* (2016.02); *G06T 2207/10081* (2013.01); *G06T 2207/10088* (2013.01); *G06T 2207/30016* (2013.01); *G06T 2207/30021* (2013.01); *G06T 2207/30101* (2013.01)

(56) References Cited

U.S. PATENT DOCUMENTS

| | | | | |
|---|---|---|---|---|
| 8,359,118 B2* | 1/2013 | Ono | ................. | G09B 23/30 434/272 |
| 2008/0234576 A1 | 9/2008 | Gavit-Houdant | | |
| 2009/0088830 A1* | 4/2009 | Mohamed | ................. | A61F 2/91 623/1.11 |
| 2011/0048433 A1* | 3/2011 | Pfister | ............. | A61B 17/12022 128/898 |
| 2012/0289777 A1* | 11/2012 | Chopra | ............. | A61B 1/00009 600/109 |
| 2013/0345719 A1* | 12/2013 | Donhowe | .......... | A61B 1/00167 606/130 |
| 2014/0005685 A1 | 1/2014 | Modrow | | |

OTHER PUBLICATIONS

Pierot, L. et al "Intrasaccular Flow-Disruption Treatment of Intracranial Aneurysms: Preliminary Results of a Multicenter Clinical Study", AJNR, American Journal of Neuroradiology, vol. 33, pp. 1232-1238. 2012.

Mut, F. et al "Effects of Flow-Diverting Device Oversizing on Hemodynamics Alteration in Cerebral Aneurysms", AJNR, American Journal of Neuroradiology, pp. 1-7, 2012.

Morales, Heman G. et al "A Virtual Coiling Technique for Image-Based Aneurysm Models by Dynamic Path Planning", IEEE Transactions on Medical Imaging, vol. 32, No. 1, pp. 119-129, Jan. 2013.

Ding, Y.H. et al "The Woven EndoBridge: A New Aneurysm Occlusion Device", AJNR, American Journal of Neuroradiology, vol. 32, No. 3, pp. 607-611, 2011.

Bernardini, Annarita et al "Influence of different computational approaches for stent deployment on cerebral aneurysm haemodynamics", Interface Focus, vol. 1, pp. 338-348, 2011.

* cited by examiner

DEPLOYMENT MODELLING

CROSS-REFERENCE TO PRIOR APPLICATIONS

This application is the U.S. National Phase application under 35 U.S.C. § 371 of International Application No. PCT/EP2014/079101, filed on Dec. 23, 2014, which claims the benefit of European Patent Application No. 14305009.4, filed on Jan. 6, 2014. These applications are hereby incorporated by reference herein.

FIELD OF THE INVENTION

The present invention relates to an image processing device for medical deployment prediction, a medical imaging system for medical device deployment prediction, a method for operating an image processing device for medical device deployment prediction, a computer program element, and a computer readable medium.

BACKGROUND OF THE INVENTION

Cerebral aneurysms are abnormal localized swellings of the wall of an artery in the brain. One method of treating such aneurysms is an endovascular intervention. The basic principle of such an intervention is to slow down the blood flow inside the aneurysm using an endovascular device for deployment. This may cause a thrombotic reaction inside the aneurysm. Known techniques for performing the endovascular intervention are, for example, coiling, or the introduction of a flow diverter. Computer-aided tools are available to plan the positioning of an endovascular device for deployment before an operation. Present procedures for endovascular planning are carried out before an endovascular intervention. Nevertheless, the incorrect placement of an endovascular device for deployment during the intervention also implies some risk. The patent publication WO 2011/121516 discusses such methods.

SUMMARY OF THE INVENTION

Therefore, there may be a need to account for the effect of incorrect placement of an endovascular device for deployment during an endovascular intervention.

According to the present invention, an image processing device for medical device deployment prediction is provided. The device comprises: an input unit, a processing unit, and an output unit.

The input unit is configured to provide to the processing unit 3D object data of a region of interest of an object. The input unit also provides 3D device model data of a device for deployment inside the object using an intervention device. Finally, the input unit provides live intervention image data of the region of interest comprising spatial information of an intervention device provided for the deployment of the device for deployment.

The processing unit is configured to localize the intervention device within the 3D object data based exclusively on a detection of the intervention device in the live intervention image data, and then to perform a spatial registration of the intervention image data and the 3D object data.

The processing unit is further configured to adapt the 3D device model data according to the 3D object data of the region of interest using the localization of the intervention device within the 3D object data, and to embed the adapted 3D device model data, representing the device for deployment, within the 3D data of the region of interest. An expected spatial relationship is generated between the device for deployment and the region of interest of the object. Finally, the output unit is configured to display the expected spatial relationship.

Advantageously, a visualization of the predicted deployment, as provided by the image processing device discussed above, provides feedback to a user about the final position of a device for deployment, in the case that it was deployed at the current localized position. This allows a user instantly to assess the relevance of the current localization of a device for deployment held on an intervention device.

Adjustments to the positioning of the intervention device may then be made, if the deployment at the current position would result in a sub-optimal positioning of the deployed device for deployment. Thus, optimal placement of the device for deployment is made more possible. This removes "guesswork" from the procedure.

In other words, a "virtual deployment" of the device for deployment is calculated, based exclusively on the intervention device's localization within the object (patient), and then displayed to the user (surgeon) on a screen during an intervention procedure.

Analysis and measurements concerning how the virtually deployed device relates to the targeted anatomy can be provided. The success of endovascular device deployment during a cerebral endovascular procedure is highly dependent on the characteristics of the position, orientation, or trajectory of the intervention device carrying the device for deployment at the time of device deployment. A localization of the intervention position of the intervention device inside the object (patient) can be performed. The localization is based only on a detection of the intervention device, regardless of whether a device for deployment is fitted to the intervention device. A calculation of the expected spatial relationship between an adapted 3D device model and the 3D data (acquired before the intervention) can be calculated. Such a calculation of the expected spatial relationship of the device for deployment when embedded within the 3D data at the localized region of the intervention device, can allow a user to identify whether the device for deployment has been positioned in the optimum position by the intervention device. Therefore, a higher likelihood of success of the endovascular procedure is possible.

According to the invention, a medical imaging system for medical device deployment prediction is also provided, comprising: an image acquisition arrangement, a device as previously described, and a display unit. The image acquisition arrangement is adapted to acquire the image data and to provide the data to the processing unit.

According to the invention, a method for operating an image processing device for medical device deployment prediction is also provided. The method comprises the steps of:

a) providing 3D object data of a region of interest of an object;

b) providing 3D device model data of a device for deployment inside the object using an intervention device;

c) providing live intervention image data of the region of interest comprising spatial information of an intervention device provided for the deployment of the device for deployment;

d) localizing the intervention device within the 3D object data based exclusively on a detection of the intervention device in the live intervention image data, and then performing spatial registration of the intervention image data and the 3D object data;

e) adapting the 3D device model data according to the 3D object data of the region of interest using the localization of the intervention device within the 3D object data; and embedding the adapted 3D device model data, representing the device for deployment, within the 3D data of the region of interest; thus generating an expected spatial relationship between the device for deployment and the region of interest of the object; and (f) displaying the expected spatial relationship.

According to the invention, a computer program element for controlling an apparatus, which, when executed by a processing unit, is adapted to perform the method steps, is provided.

According to the invention, a computer readable medium having stored the program element discussed previously is provided.

It can therefore be seen that a virtual deployment condition based exclusively on a detection of a measured position, and/or orientation, and/or trajectory of the intervention device is displayed to a user. The intervention device can form the delivery system of a device for deployment inside an endovascular network. It is not necessary for the device for deployment to be present for the localization of the intervention device to be performed. Such a system combines the previously known anatomical geometry of a patient with a model of the device for deployment. The geometry data forming the 3D object data can be obtained via a CT scan or any other imaging system capable of providing a 3D representation of the vasculature of an object (patient). The geometry data can, for example, be loaded from a storage server or a disc before a procedure.

A model of the device for deployment inside the patient obtained prior to the procedure, for example from manufacturer datasheets, or laboratory measurements is provided. The model may be expressed in a data format, which describes the geometrical and/or mechanical relationship of a device for deployment in-between its undeployed and deployed positions. Thus, the model may be stored on a server, loaded from a disk, or downloaded from a manufacturer's website. The system also provides means for localizing an intervention device. Such a means may be with bi-plane acquisition, or electro-magnetic localization. Means to project, display, or to indicate the deployment results according to the current localization of the delivery system are also provided.

In this description, the term "3D object data" defines data acquired, for example, by a CT scanner, or by an MRI scanner, containing information about at least the structure of a patient's blood vessels. The data may be stored on a disk, or loaded from a server, for example.

The term "3D device model data" defines a virtual model of a device for deployment inside a patient. This data can be obtained from manufacturer information, 3D imaging, and laboratory measurements, or a combination of these. Such a model of the device for deployment defines, mathematically, the relationship between members constituting the device, as it moves from an un-deployed position to a deployed position. Of course, the model may be a detailed finite-element model expressing the dynamic mechanical relationship between the members. Alternatively, a simplified model, relying only on geometry, may be used.

The term "live intervention image data" refers to an image, which is taken in real-time during an intervention procedure, during the positioning of a device inside a patient. Typically, the live intervention image data will show the current position of an intervention device. Optionally, markers, such as radio-opaque markers, may be used on the intervention device to enable easier localization.

Thus, the localization is performed exclusively using the intervention device, and not using a device for deployment fitted to the intervention device.

Typically, the live intervention image data is obtained using bi-plane localization. Any localization method may be used, however, provided it enables the localization of an intervention device during an endovascular procedure.

The term "spatial registration" refers to the creation of a geometrical relationship between the 3D object data and the intervention image data. The 3D object data is, typically, static, because it has been acquired before the intervention procedure. The live intervention image data is, typically, not static, because it is acquired in real-time. The 3D object data and the live intervention image data is acquired using different modalities. Therefore, there is a need to transform the geometry of the 3D object data into the geometrical framework of the intervention image data (or vice-versa) to enable a combination of the information contained in both images. Such a step is carried out using spatial registration between the 3D object data and the intervention image data, a technique known to those skilled in the art.

The term "embed the adapted 3D device model data" signifies the process of adapting a mesh, or set of coordinates defining the 3D device model, until the device model has been reshaped such that it is coincident with features of the 3D object data. Such a process may be carried out iteratively, and/or using geometric solving methods, or finite-element methods, for example. Many techniques usable to adapt a 3D device model to the 3D object data, are applicable.

The term "generating an expected spatial relationship" refers to a process of solving iteratively the equations defining the boundary provided by the vasculature in the 3D object data, and the equations defining the constraints of the 3D device data. Thus, the 3D object data will represent at least a blood vessel, which will provide a boundary condition for the expansion of the 3D device model data from its starting position at a localized position inside the vessel.

The term "expected spatial relationship" can refer to the final position of the deployed device for deployment with respect to the boundary conditions imposed by the vessel, and the localized position of the intervention device, which is the starting point of the virtual deployment. It is to be understood that because the deployed position of the virtually deployed device for deployment will, in reality, have to conform, or at least take into account, the vessel shape, the virtually deployed device will have a complex shape. Thus, the expected spatial relationship will, necessarily, be of a complex nature. In one example, a net-list of a geometrical net of the device for deployment could comprise thousands of points. Each point will conform to a boundary condition imposed by the vessel, perhaps with respect to a mechanical constraint of the device for deployment's model.

The term "intervention device" refers to a device, which is used in an endovascular intervention to deliver an un-deployed device for deployment inside an object (patient), such as an un-deployed stent, or a wire coil, to a region of interest where the device for deployment should be deployed. This could be a catheter, or another type of stent delivery system or wire coil delivery system. The intervention device may be inserted into the object (patient) and manoeuvred to the region of interest by the user. In an example, the intervention device may contain markers, which are detectable using X-ray or electromagnetic means. Such markers can allow improved localization of the intervention device. The intervention device can be inserted into a patient without a device for deployment visible. In the case of a stent, this means, for example, that the undeployed stent is not attached to the end of the intervention device. In the case of wire-coil delivery systems, the wire coil will, naturally, not be visible when held inside the intervention device.

The term "region of interest of an object" refers to an area, in which an intervention process involving the placement of a device for deployment using an intervention device takes place inside a human body. An intervention region may contain an aneurysm, for example.

The discussion of a "user" in this specification refers to a medical professional, such as a surgeon.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
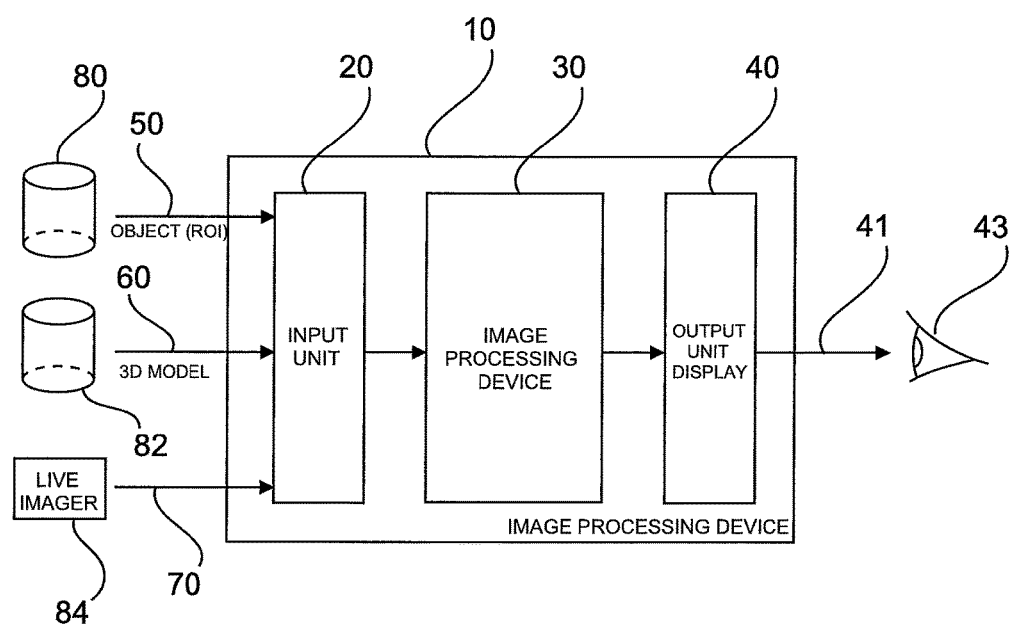
FIG. 1 shows an image processing device for medical device deployment prediction.

FIG. 1 shows an image processing device 10 for medical device deployment prediction, comprising an input unit 20, a processing unit 30, and an output unit 40.

The input unit is configured to provide to the processing unit 30 3D object data 50 of a region of interest of an object, 3D device model data 60 of a device for deployment inside the object using an intervention device, and live intervention image data 70 of the region of interest comprising spatial information of an intervention device provided for the deployment of the device. The processing unit 30 is configured to localize the intervention device within the 3D object data, based exclusively on a detection of the intervention device in the live intervention image data, then to perform a spatial registration of the intervention image data and the 3D object data. The processing unit 30 is configured to adapt the 3D device model data according to the 3D object data of the region of interest, using the localization of the intervention device within the 3D object data, and then to embed the adapted 3D device model data, representing the device for deployment, within the 3D data of the region of interest. This generates an expected spatial relationship between the device for deployment and the region of interest of the object. The output unit 40 is configured to display the expected spatial relationship.

The input unit may provide the 3D object data and the 3D device model data from external databases 80 and 82. Alternatively, this data may be stored on disks, uploaded from USB devices, or downloaded from the internet. Many ways of providing this data will be known to the skilled person.

The 3D object data is a voxel-based model of the anatomy of an object of interest (patient), or any other representation that allows 3D reconstruction of the vessel arrangement of a region of interest of an object (patient). Such data is acquired using a CT scanner although other techniques will be known.

The intervention image data is provided from, for example, a bi-plane localization using two X-ray C-arm images. The bi-plane localization technique is well-known to those skilled in the art.

In practical terms, the processing unit 30 may be any means suitable for processing the data input from the input unit 20. Thus, a computer with an appropriate specification could be used. A computer equipped with means to accelerate certain calculations may be provided, such as parallel processors, or FPGA or GPU co-processors.

The output unit 40 may comprise a conventional computer monitor or projection screen for displaying the expected spatial relationship (virtual deployment result) at certain intervention device localizations. The virtual deployment may be super-imposed on a synthetic reconstruction of the 3D data, or an internal position of the vessel geometry. Alternatively, the virtual deployment may be superimposed on the live 2D image obtained by bi-plane imaging.

Figures 2A, 2B:
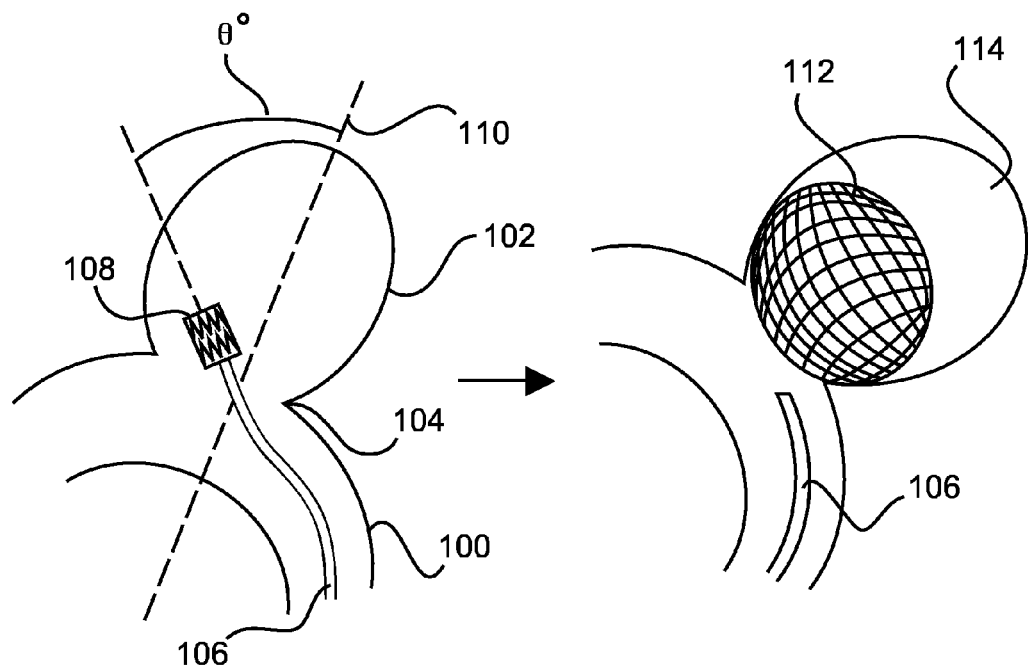
FIG. 2 shows examples of device deployment in an endovascular intervention.

An issue facing a user (a surgeon) when placing a device for deployment inside an aneurysm, is illustrated in FIGS. 2A to 2D. FIG. 2A shows a blood vessel or artery 100 with an aneurysm 102. The aneurysm is attached to the blood vessel at the neck (ostium), indicated with a reference 104. As can be seen, an intervention device 106 is inserted inside the blood vessel and is moved by a user up towards the aneurysm 102. The intervention device may, for example, be a catheter. Mounted on the end of the intervention device is an un-deployed device for deployment 108. Defined with a dotted line 110 is a major axis of the aneurysm.

In this hypothetical example, as can be seen in the example of FIG. 2A, the intervention device is angled at a significant deviation, θ degrees away from the major axis 110. The effect of deploying the device for deployment in this position is shown in FIG. 2B. This also shows the intervention device after deployment. The intervention device is, now, not connected to the deployed device for deployment. The deployed device for deployment is shown at 112. It can be seen, however, that there is a large space 114 inside the aneurysm 102, which results because the device for deployment was deployed at a large angle away from the optimal deployment angle.

The situation illustrated in FIG. 2B is problematic. The deployed device for deployment could become dislodged from the aneurysm over time. In addition, the deployed device for deployment might not function to staunch the blood flow from the blood vessel 100 into the aneurysm 102. If that was the case, a thrombotic reaction would not occur inside the aneurysm, and the procedure would be deemed to have failed.

Figures 2C, 2D:
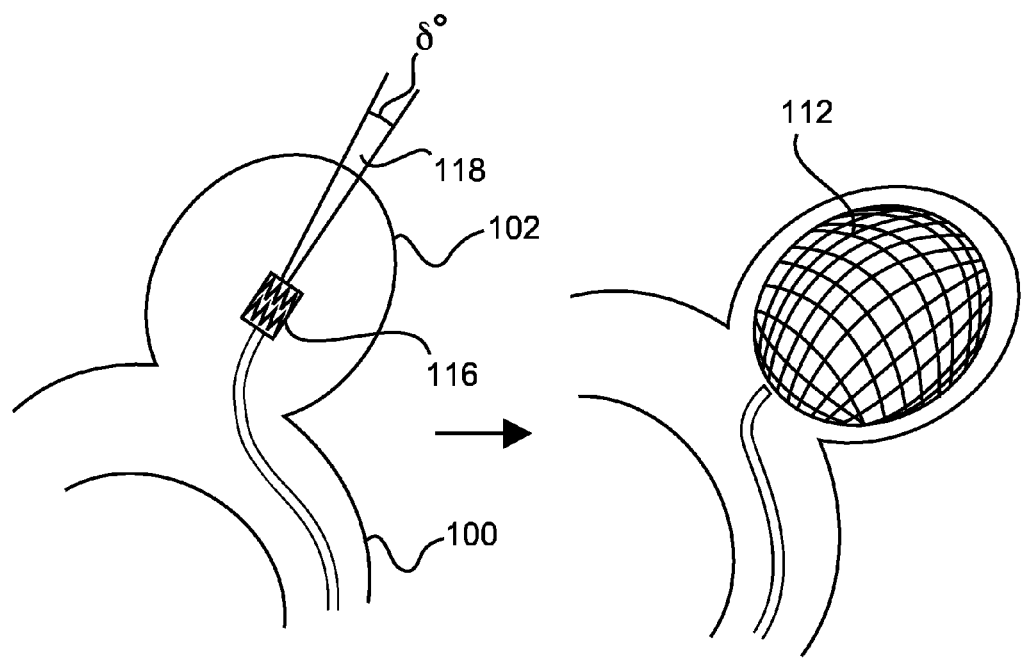

FIG. 2C illustrates a device for deployment 116 that is shown inside the blood vessel 100 before deployment into the aneurysm 102. In this case, an angle of divergence 118, δ degrees is much smaller than as shown in FIG. 2A. The device for deployment in its un-deployed position has been aligned substantially with the major axis of the aneurysm. It would, hypothetically, be advantageous to deploy the device for deployment as close to the dotted line of the major axis of the aneurysm as possible, owing to the characteristics of the hypothetical illustrated device for deployment.

Thus, as shown in FIG. 2D, when the user chooses to deploy the device for deployment 112, it can be seen that there is substantially no gap between the boundary of the deployed device for deployment and the wall of the aneurysm. Advantageously, this means that the device for deployment has been correctly deployed, and can function, as intended, to cause a thrombotic reaction inside the aneurysm, thus successfully staunching the blood flow.

Of course, other devices for deployment are known. For example, a coil can be inserted into the aneurysm to slow down the blood flow. A stent can be placed covering the entry of the aneurysm in the blood vessel 100. It will be appreciated that in all of these cases, the key issue is whether or not the intervention device has been positioned with the correct orientation, in order to allow a thrombotic reaction to occur within the aneurysm.

It should be appreciated that different types of devices for deployment will, necessarily, have different optimum deployment conditions in relation to the intervention device and the 3D object data. The above example should not be interpreted as limiting the technique described herein to one optimum deployment condition, but rather, to the optimum deployment condition relevant to the appropriate device for deployment when used in an intervention.

Figure 3A:
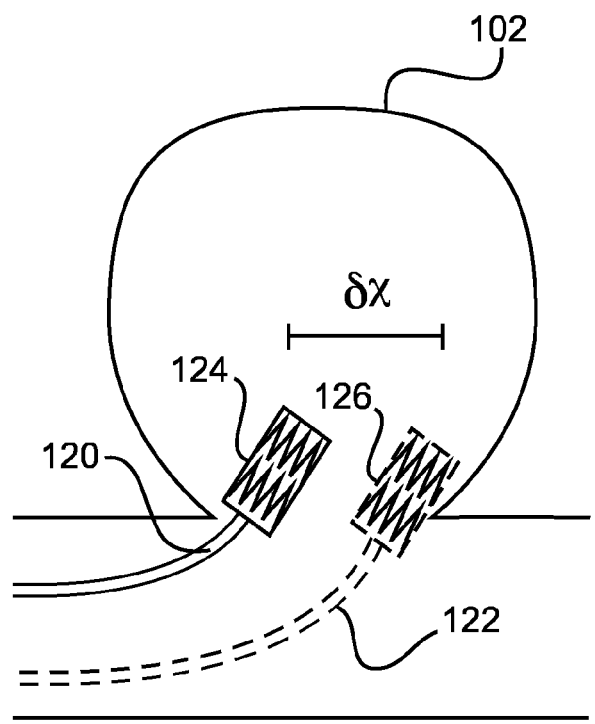
FIG. 3 further shows possible deployment modalities in an endovascular intervention.

FIG. 3A illustrates one possible variation of the position of the intervention device. In FIG. 3A, an intervention device 120 is shown at an offset to another position of an intervention device 122, shown in dotted lines. Respective undeployed devices for deployment 124 and 126 are shown separated by a linear distance δx. Thus, when deployed inside the aneurysm, the distance δx could cause a difference in deployment shape.

Figure 3B:
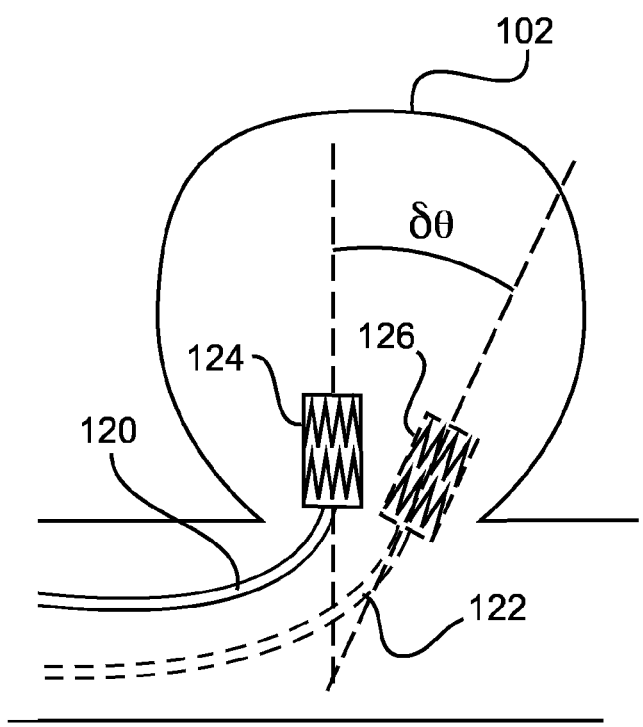

An alternative situation is shown in FIG. 3B. The intervention device 120 and the intervention device 122 are shown entering the aneurysm 102 at differing angles. The difference between the positions is δθ degrees. This angular variation in deployment position can also cause a misplacement of the device for deployment. Another situation that can be conceived, but which is not illustrated, is that, in which the intervention devices 120 or 122 have followed a different trajectory into the aneurysm. Of course, it will be understood by a person skilled in the art that, usually, only a single intervention device is usually present within the aneurysm at one time, and that the display of a plurality of intervention devices in the figures is merely to show their different deployment positions.

The operation of the processing unit 30 is best described below in relation to the method, which is performed on the data from the input unit 20.

According to an embodiment of the invention, an example of the image processing device 10 is provided as previously described, wherein the input unit 20 is further configured to receive a display command from a user. The processing unit 30 is further configured to generate, and display, the expected spatial relationship upon reception of the display command. Therefore, in this embodiment, it is possible for the user to define the moment, at which the output unit displays the expected spatial registration between the device for deployment and the 3D object data of the object.

The expected spatial relationship may not be displayed for most of the procedure, and at other points, at which the device for deployment was almost in a deployment position, the medical professional could trigger the display of the expected spatial registration between the deployed device for deployment and the 3D object data of the object. The display of the expected spatial registration may, for example, be achieved with a "ghosting" technique, wherein a semi-translucent impression of the deployed device for deployment in its current deployment position as defined by the localized intervention device is shown. In this way, the user is provided with a clear impression of the deployed device for deployment at the localized position, but can still view the vasculature.

According to an embodiment of the invention, an example of the image processing device 10 is provided, wherein the processing unit 30 is further configured to monitor the live intervention image data of the intervention device, and configured to generate the expected spatial registration when a change of the live intervention image data of the intervention device is below a triggered threshold.

The continuous display of the expected spatial registration between the 3D object data and the deployed device for deployment within the region of interest may not always be required. For example, the intervention device must travel a long way through the vasculature before it arrives at the deployment site, such as an aneurysm. Therefore, in this embodiment, the expected spatial relationship between the deployed device for deployment and the 3D object data is not displayed until the change of the live intervention image data is below a triggered threshold, for example the intervention device may move at a lower speed, signifying that the intervention device has come to a stop in front of the deployment site.

For example, the processing unit is configured to monitor the live intervention image data of the intervention device, and to generate the expected spatial relationship when a change of the speed of the device for deployment is below a trigger threshold.

In another example, the processing unit is configured to monitor the live intervention image data of the intervention device, and to generate the expected spatial relationship when a change of the intervention device in the line intervention data exceeds a trigger threshold, e.g. is below a trigger threshold.

According to an embodiment of the invention, an example of the image processing device 10 is provided, wherein the processing unit is configured to monitor the live intervention image data of the intervention device, and configured to generate the expected spatial registration when a change of the live intervention image data of the intervention device exceeds a triggered threshold.

According to an alternative, the live intervention image data may show that the localization of the intervention device with respect to the aneurysm exceeds a triggered threshold. For example, in this embodiment, if the deployment angle of the undeployed device for deployment exceeds a threshold, which would cause the expected spatial registration between the aneurysm in the 3D object data and the deployed aneurysm to disadvantageously be too large, the expected spatial registration between the deployed device for deployment and the 3D object data would be displayed to provide a warning to the user.

According to an alternative, the image processing device 10 is provided, wherein the processing unit is configured to monitor the live intervention image data of the intervention device, and configured to generate the expected spatial registration when a change of the live intervention image data of the intervention device lies in-between a lower trigger threshold and an upper trigger threshold.

According to an alternative, a change of the live intervention image data denotes a change of the localization of the intervention device within the intervention image data.

According to an embodiment of the invention, an example of the image processing device 10 is configured to provide final optimal deployment data of the device for deployment to the processing unit.

The processing unit 30 is further configured to calculate i) a difference metric between the final optimal deployment position data of the device for deployment, and the adapted 3D device model data according to the 3D object data of the region of interest, using the localization of the intervention device within the 3D object data. The processing unit 30 is further configured to calculate ii) a difference metric between the final optimal deployment position data of the device for deployment and the adapted 3D device model data. The output unit 40 is configured to display the difference metric between a final optimal deployment position of the device for deployment and the adapted 3D device model data.

In this embodiment, the input unit 20 is, additionally, configured to provide final optimal deployment position data of the device for deployment to the processing unit 30. This may come, for example, from the virtual positioning of a 3D device model inside the 3D object data before a clinical procedure begins. Then, the user has enough time to consider an optimal positioning of the device for deployment. This data is stored and, optionally, displayed on the output unit 40 during an endovascular procedure. The localization of the intervention device, and the live calculation of the deployment state of a 3D device model at that localized position is possible. Therefore, it is also possible to compare the final optimal deployed position selected before the endovascular procedure with the current deployed position during the endovascular procedure. Hence, a simplified metric 130 can, optionally, be provided to the user on the output unit 40.

The metric is, for example, a percentage optimality between the optimal deployment position selected by the user before the endovascular procedure, and the adapted 3D device model data resulting from the current localization of the intervention device. Such a difference metric, could, for example, be calculated by registering positions on the external body of the localized 3D device model in its current deployment position with the same points on the final optimal deployment position data of the device for deployment. The volume enclosed by such a registered relationship represents the current difference between the optimal position and the localized position of the intervention device. Therefore, by integrating this volume in space, the percentage optimality of the placement can be calculated. Of course, there are diverse ways of assessing and calculating such an optimality metric.

According to an embodiment of the invention, an example of the image processing device 10 is provided, wherein the output unit is configured to display a representation of a first device for deployment in a final optimal deployment position of the device for deployment in the 3D object data of a region of interest, and to display a representation of a second device for deployment in a position defined by the localization of the intervention device, in the 3D object data of a region of interest, wherein the position of the second device for deployment is displayed according to the expected spatial relationship between the second device for deployment and the region of interest of the object.

Figure 4:
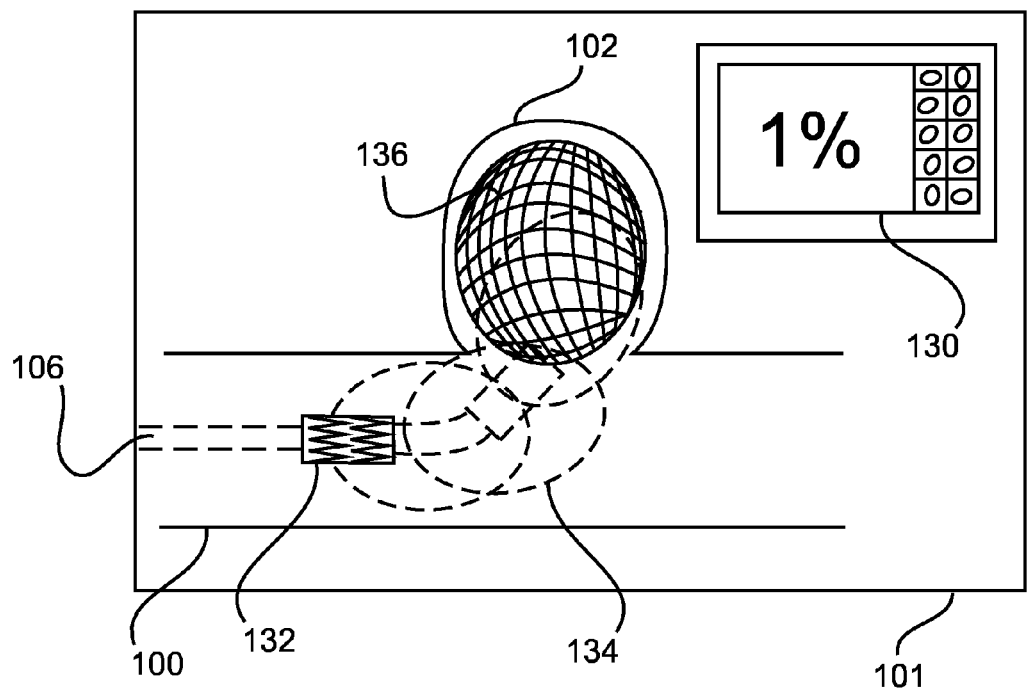
FIG. 4 shows an endovascular intervention.

FIG. 4 shows a screen of the output unit 40 during a deployment scenario. The blood vessel 100 and the intervention device 106 are shown with an undeployed device for deployment 132. The expected spatial relationship is calculated and shown at 134. The dotted impressions 134 signify that the expected spatial relationship is constantly being updated and displayed during the deployment scenario to aid the user in the placement decision. The final optimal deployment position 136 inside the aneurysm 102 can also be displayed, as shown.

This optimal placement has been decided before an endovascular procedure by a medical professional using a virtual device placement technique.

Virtual device placement may be carried out before an intervention. 3D object data may be loaded onto a computer screen, and displayed to a user. The user may select a device for deployment from a list of appropriate devices. Then, using the computer interface (mouse, keyboard, joystick, touch-screen) the user may position the device for deployment inside the 3D object data, as displayed. The virtual device placement may model the device in its deployed position at a selected point inside the 3D object data. The user may reposition the model in the 3D object data until an optimal placement is attained.

The difference metric 130 is calculated as described previously, although it will be appreciated that there are many different ways of calculating, and displaying, such a difference metric. In FIG. 4, the optimality metric shows 1 percent, because deployment of the device for deployment at the "current" position indicated with the reference 132 of the undeployed device for deployment would result in a very poor match, compared to the optimum case defined prior to the endovascular intervention using "virtual device deployment".

Therefore, according to this embodiment, although it is possible to display a difference metric, a real representation can also be displayed, so that a user can obtain an anatomical view of the optimality of the placement of the device for deployment compared to the final optimal deployment position of the device for deployment selected before the operation.

Thus, advantageously, the benefits of "virtual device deployment" before an endovascular procedure are augmented, by allowing the optimal placement determined before an endovascular intervention to be exploited during an endovascular intervention, by monitoring the intervention device's localization, as determined from the live intervention image data 70.

In an alternative, it will be appreciated that audio feedback may be provided to the user when a certain level of placement optimality is reached.

According to an embodiment of the invention, the processing unit 30 is configured to use the live intervention image data to calculate the localization data, wherein the localization data is selected from the group of:
i) the instantaneous position of the intervention device relative to the region of interest;
ii) the instantaneous orientation of the intervention device relative to the region of interest;
iii) a prior trajectory of the intervention device; or
iv) any combination of i) to iii).

As discussed previously, the live intervention image data may be used to calculate many different types of localization data enabling localization of the intervention device. These positions, orientations, or trajectories may be calculated using image processing techniques known to those skilled in the art.

According to an alternative, the particular form of the undeployed device for deployment may be used to improve the robustness of the detection of the position of the intervention device.

According to an embodiment of the invention, an example of the image processing device 10 is provided according to the previous description, wherein the intervention device is a practice device.

A "practice device" refers to an intervention device without a device for deployment fitted. Advantageously, a user may practice the deployment of a device for deployment during an intervention procedure prior to the procedure, in which a device for deployment is to be placed. The image processing device according to this embodiment may enable a live display of the device for deployment in its position according to the expected spatial relationship between the localized practice device, and the 3D object data. The ability to display the predicted deployment in a prior procedure, could, advantageously, allow a user to practice the deployment to ensure that unexpected eventualities would not occur in the real deployment.

According to the invention, the intervention device may for example be delivery system.

The delivery system can be used to place a device for deployment, such as a balloon catheter, a constrained-sheath system (which allows a coiled stent to expand when the sheath is pulled off), an embolic coil delivery system, a woven endobridge delivery system, or another such device for deployment known in the art. Therefore, the delivery system may be tracked inside a patient's vasculature, even, when a device for deployment is not fitted to it (or when a coil is not deployed by it). This allows a clinical professional to "practice" the deployment of a device for deployment at the appropriate location inside a patient using the appropriate delivery system, and to examine the virtually-generated final resting position of the virtually deployed delivery system, without using (and thereby "spoiling") a real device for deployment. In this way, unforeseen issues affecting the deployment of a stent, or coil, resulting from the interaction of the patient's vasculature and the delivery system, may be foreseen.

According to an embodiment of the invention, an example of the image processing device 10 is provided, where the live intervention image data of the localization of the intervention device is from a bi-plane acquisition.

Bi-plane acquisition can be used to localize the intervention device. It is performed using detection and tracking in two planes, and simple 3D image registration. The bi-plane data can be obtained, for example, using two C-arms intersecting the region of interest in the patient. Using bi-plane image acquisition, it is possible to track the 2D location of an object in the images separately in each plane. Through a combination of the 2D coordinate information of each plane, the 3D position of the intervention device in the object can be derived.

According to an embodiment of the invention, an example of the image processing device 10 is provided, wherein the live intervention image data of the localization of the intervention device is from an electro-magnetic localizer. An electro-magnetic localizer allows the 3D tracking of an intervention device in real-time, using electro-magnetic means.

According to an embodiment of the invention, an example of the image processing device 10 is provided, wherein the device for deployment is selected from the group of flow diverters, coils, woven endobridges, Luna™ valves, hear valve prostheses, stents, or balloons.

It will be appreciated that the devices for deployment may be deployed inside the aneurysm, and may, therefore be referred to as "intra-saccular". Alternatively, the devices for deployment may be deployed outside an aneurysm, and may, therefore, be referred to as "exo-saccular".

A flow diverter is a single endovascular stent device capable of redirecting blood flow away from an aneurysm. This is achieved by positioning the stent device outside an aneurysm. The effective deployment of flow diverting stents depends on factors such as position in relation to the geometry of the parent vessel, correct sizing, and the degree of opening.

Alternatively, the device for deployment may be a coil. Coiling is a popular endovascular therapy to treat cerebral aneurysms. The procedure involves the insertion of small and thin biocompatible metal wires that partially fill the aneurysm cavity. By reducing flow velocities, coils alter the intra-aneurismal haemo-dynamics. By increasing blood residence times, thrombus formation may be triggered.

According to an alternative, a device for deployment may be a woven endobridge. Unlike a flow diverting stent, which is positioned in the main blood vessel and not in the aneurysm, a woven endobridge is positioned within the aneurysm cavity, as illustrated in FIG. 2D. Similar to the woven endobridge is the "Luna"™ aneurysm embolization system.

In the foregoing description, reference has been made to the modelling of an expected spatial relationship between a device for deployment in a cerebral aneurysm. It will, though, be appreciated that the technique described herein is broadly applicable to any situation, in which a device is introduced into, and expanded within the vasculature.

According to the invention, a medical imaging system 150 for medical device deployment prediction may be provided.

The medical imaging system 150 comprises: an image acquisition arrangement 152, an image processing device for medical device deployment prediction as previously described, and a display unit 156.

The image acquisition arrangement 152 is adapted to acquire the image data and to provide the data to the processing unit.

Figure 5:
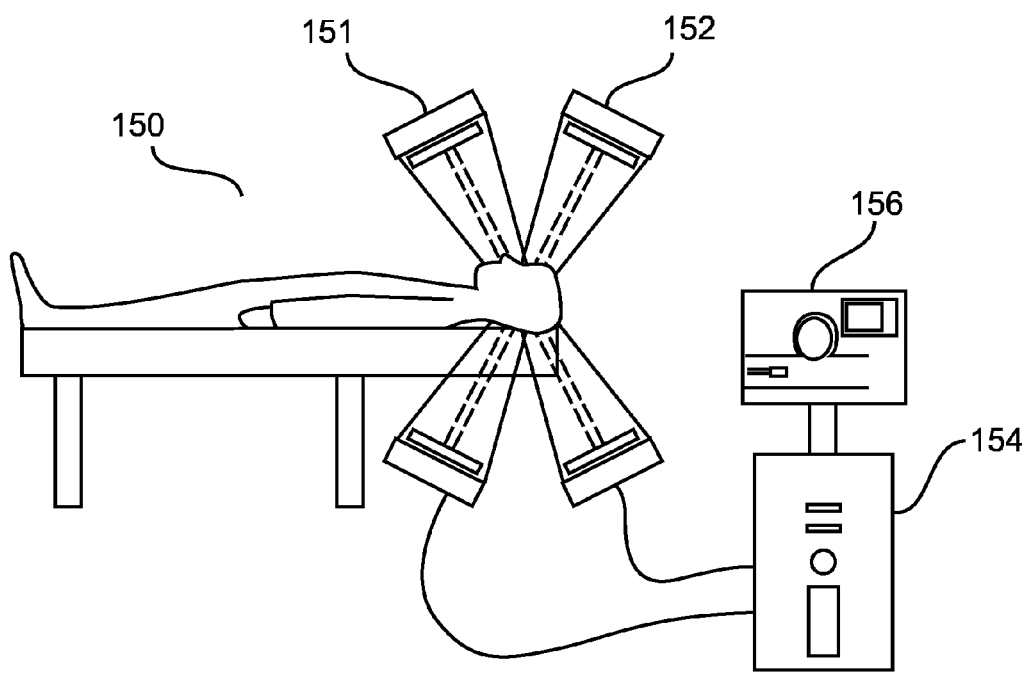
FIG. 5 shows a medical imaging system.

FIG. 5 illustrates a system as described above, and shows X-ray image acquisition arrangements 151 and 152 with an X-ray source and an X-ray detector. These devices may be mounted on C-arms, for example. The devices are shown suitable for performing a bi-plane live image acquisition. The image acquisition arrangement is a movable system with an X-ray source mounted on a support, a portable detector that can be arranged below a patient lying on a bed with a lifted support portion. Other X-ray systems can be used, such as fixedly mounted systems or systems with source and detector mounted to movable portions, such as robotic arms. The X-ray image acquisition devices are connected to the processing unit 154. The processing unit 154 outputs an image or video sequence to a display unit 156.

In an example, the image acquisition device provides pixel area information to the processing unit.

Figure 6:
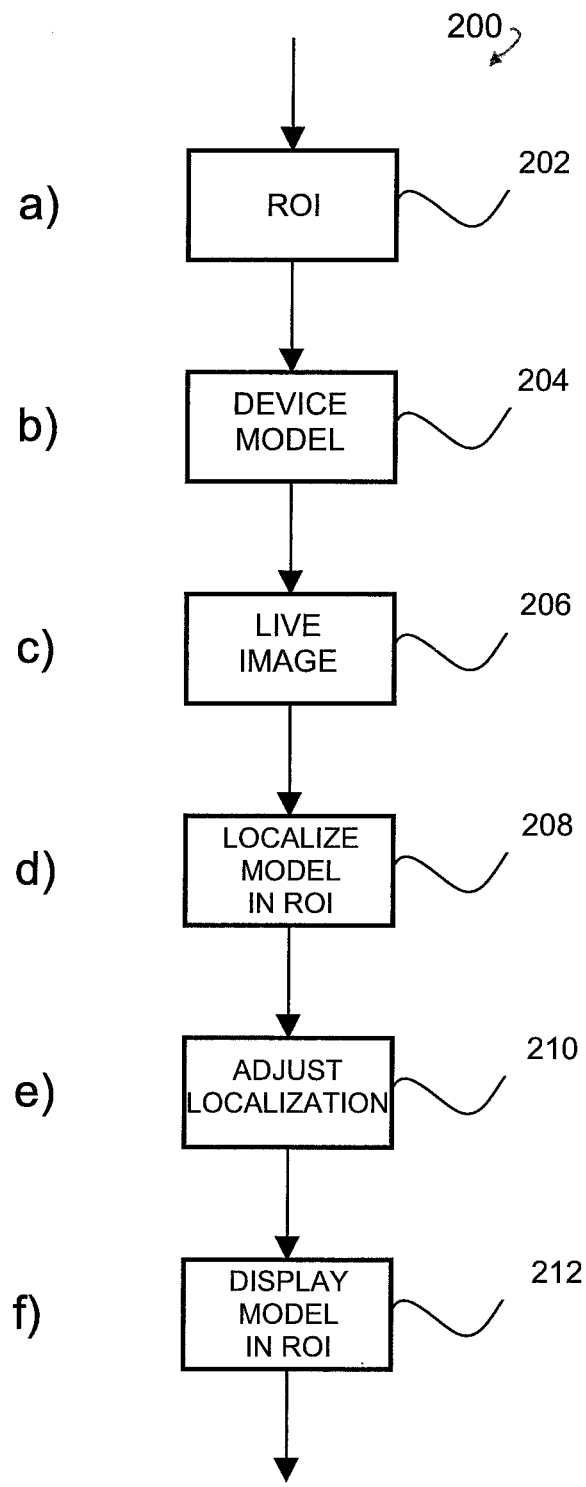
FIG. 6 shows a method for operating an image processing device for medical device deployment prediction.

As shown in FIG. 6, there is also provided a method 200 for operating an image processing device for medical device deployment prediction. The method comprises the steps of:
a) providing 202 3D object data of a region of interest of an object;
b) providing 204 3D device model data of a device for deployment inside the object using an intervention device;
c) providing 206 live intervention image data of the region of interest comprising spatial information of an intervention device provided for the deployment of the intervention device;

d) localizing 208 the intervention device within the 3D object data based exclusively on a detection of the intervention device in the live intervention image data, and then performing a spatial registration of the intervention image data and the 3D object data;

e) adapting 210 the 3D device model data according to the 3D object data of the region of interest using the localization of the intervention device within the 3D object data; and embedding the adapted 3D device model data, representing the device for deployment, within the 3D data of the region of interest; thus generating an expected spatial relationship between the device for deployment and the region of interest of the object; and (f) displaying 212 the expected spatial relationship.

In step a), the 3D object data of a region of interest of an object is typically available from pre-interventional data obtained from a CT scan, or from a PERI-interventional reconstruction, such as C-arm CT vascular reconstruction. This 3D representation should contain the landing-spot of the device for deployment, and its vascular surroundings. For example, in neuro-endovascular surgery, it could be the 3D geometry of the aneurysm and the attached surrounding vessels.

In step b), the 3D device model data of a device for deployment inside the object using an intervention device, wherein the device is an endovascular device, can be obtained from manufacturer information, 3D imaging, and laboratory measurements, or a combination of these. The 3D device model data provides information on the evolution of the geometric or mechanical arrangement of a device for deployment inside the object between an undeployed and a deployed state.

In step c), the live intervention image data of the region of interest may be provided, for example, using a bi-plane imaging method. Such an imaging method is carried out during an endovascular intervention operation. The intervention device is visible in both planes of the bi-plane acquisition. It is detected and tracked in real-time. A simple model of the delivery system can then be built in three dimensions, thus providing the position, orientation, and trajectory of the intervention device inside the relevant vasculature.

In step d), the localization is performed exclusively on the basis of a detection of the intervention device. Therefore, the device for deployment (for example, an undeployed stent, wire coil, or woven endobridge) does not need to be detected in order for the localization to be performed. Advantageously, this means that a device for deployment does not need to be deployed, or does not need to be fitted, to the intervention device in order for a medical professional to determine an impression of the final position of the device for deployment.

In an alternative, the active localizer means can be provided using electromagnetic tracking.

In an alternative, the 3D geometry data of the object to be imaged and the 3D device model data, when not yet deployed, can be used, in association with an image processing algorithm, to improve the robustness of the localization of the intervention device during an intervention.

Thus, having the 3D object data, 3D device model data, and the live intervention image data, which produces a live localization of the intervention device as described previously, it is possible to track the location of the intervention device within the 3D object data in real-time and base a virtual deployment exclusively upon the position of the intervention device in the patient.

Through the application of an arithmetic method to simulate the deployment of the device for deployment from its undeployed position to its deployed position, an expected spatial relationship between the device for deployment and the region of interest of the object can be generated. In practice, to simulate the evolution from undeployed to deployed position of the device for deployment, a fast solver for virtual deployment may be provided with the 3D object data representing patient anatomy, with the localization results of the intervention device and with the 3D device model data. It will be understood by the skilled person that a fast result from the virtual deployment is desirable, because it is convenient of the expected spatial registration is displayed with a minimal delay in a clinical situation.

In an alternative, the expected spatial registration would be available whenever the intervention device was manoeuvred, by detecting a rate of change of the position, angle, or trajectory of the intervention device, for example. In order to achieve this, a fast solver can be used to update the expected relationship constantly. Such as fast solver can use the geometrical data of the 3D object data representing the patient anatomy and the 3D device model data.

In an alternative, a finite element solution method may be applied.

Virtual deployment may be faster with a geometry-based device modelling, because no mechanical properties need to be simulated.

In step f) of the previously described method, the step of displaying the expected spatial registration enables the virtual deployment result of the device for deployment to be visualized at the current localized position of the intervention device. This provides feedback on the relevance of the current delivery localization.

It will be appreciated that the method according to the invention is executed on the processing unit of the image processing device according to the invention as described previously.

According to an aspect the invention, a method is provided for operating an image processing device for medical device deployment prediction, comprising the steps of:

a) providing 3D object data of a region of interest of an object;

b) providing 3D device model data of a device for deployment inside the object using an intervention device;

c) providing live intervention image data of the region of interest comprising spatial information of an intervention device provided for the deployment of the device for deployment;

d) localizing the intervention device within the 3D object data based exclusively on a detection of the intervention device in the live intervention image data, and then performing a spatial registration of the intervention image data and the 3D object data;

e) adapting the 3D device model data according to the 3D object data of the region of interest using the localization of the intervention device within the 3D object data; and embedding the adapted 3D device model data, representing the device for deployment, within the 3D data of the region of interest; thus generating an expected spatial relationship between the device for deployment and the region of interest of the object; and (f) displaying the expected spatial relationship.

Advantageously, the method according to the invention can be used to display the expected spatial registration between a device for deployment in its undeployed state at a localized position within 3D object data representing a region of interest of an object. In an example, the object may be a human body. In an example, the region of interest may be an aneurysm, a cerebral aneurysm, or a region of the human body where a device for deployment must be placed.

It will be appreciated that the provision of the data in steps a), b), and c) may occur in any order without detriment.

There now follow several further embodiments defining exemplary steps that may be used in conjunction, or in combination with the above defined method.

According to a first embodiment, there is provided a method for operating an image processing device for medical device deployment prediction, comprising the steps of:
a) providing 3D object data of a region of interest of an object;
b) providing 3D device model data of a device for deployment inside the object using an intervention device;
c) providing live intervention image data of the region of interest comprising spatial information of an intervention device provided for the deployment of the device for deployment;
d) localizing the intervention device within the 3D object data based exclusively on a detection of the intervention device in the live intervention image data and then performing a spatial registration of the intervention image data and the 3D object data;
e) adapting the 3D device model data according to the 3D object data of the region of interest using the localization of the intervention device within the 3D object data; and embedding the adapted 3D device model data, representing the device for deployment, within the 3D data of the region of interest; thus generating an expected spatial relationship between the device for deployment and the region of interest of the object; and
f) displaying the expected spatial relationship.

According to a second embodiment of the method, there is provided a method according to the first embodiment, further comprising, between step b) and step c), a step
b1) receiving a display command from a user; and
wherein, in steps d) and step e), the generation of the expected spatial relationship is performed upon reception of the display command.

According to a third embodiment of the method, there is provided a method according to the first or second embodiment, further comprising, between step d) and step e), a step:
d1) monitoring the live intervention image data of the intervention device, and
wherein, in steps e) and f), the generation of the expected spatial relationship is performed when a change of the position of the intervention device in the live intervention image data is below a trigger threshold.

According to a fourth embodiment of the method, there is provided a method according to one of the first to third embodiments, further comprising, between step d) and step e), a step:
d2) monitoring the live intervention image data of the intervention device;
wherein, in steps e) and f), the generation of the expected spatial relationship is performed when a change of the deployment angle of the of the intervention device in the live intervention image data of the intervention device exceeds a trigger threshold.

According to a fifth embodiment of the method, there is provided a method according to one of the first to fourth embodiments, wherein in-between steps b) and c) there is provided a further step:
b2) providing final optimal deployment position data of the device for deployment;

wherein in-between step e) and step f) are the steps of:
e1) calculating a difference metric between the final optimal deployment position data of the device for deployment, and the adapted 3D device model data according to the 3D object data of the region of interest using the localization of the intervention device within the 3D object data;
e2) calculating a difference metric between the final optimal position data of the device for deployment and the adapted 3D device model data; and
wherein step f) further comprises:
f1) displaying the difference metric between the final optimal deployment position of the device for deployment and the adapted 3D device model data.

According to a sixth embodiment of the method, there is provided a method according to the fifth embodiment, wherein the step f) further comprises:
f2) displaying a representation of a first device for deployment in the final optimal deployment position of the device for deployment in the 3D object data of a region of interest; and
f3) displaying a representation of a second device for deployment in a position defined by the localization, in the 3D object data of a region of interest;
wherein the position of the second device for deployment is displayed according to the expected spatial relationship between the second device for deployment and the region of interest of the object.

According to a seventh embodiment of the method, there is provided a method according to one of the first to sixth embodiments, wherein in step e), the calculation of the localization data is performed by localization data represented by:
e3) the instantaneous position of the intervention device relative to the region of interest; or
e4) the instantaneous orientation of the intervention device relative to the region of interest; or
e5) a prior trajectory of the intervention device; or
e6) any combination of localization data in steps e3) to e5).

According to an eighth embodiment of the method, there is provided a method according to one of the first to seventh embodiments, wherein in step c), the intervention device is a practice device.

According to a ninth embodiment of the method, there is provided a method according to one of the first to eight embodiments, wherein in step c), the live intervention image data of the localization of the intervention device is from a bi-plane acquisition.

According to a tenth embodiment of the method, there is provided a method according to one of the first to ninth embodiments, wherein in step c), the live intervention image data of the localization of an intervention device is from an electro-magnetic localizer.

According to an eleventh embodiment of the method, there is provided a method according to one of the first to tenth embodiments, wherein the device for deployment is selected from the group of: flow diverters, coils, stents or a woven endobridge.

According to a twelfth embodiment of the method, there is provided a method according to one of the first to eleventh embodiments, wherein the intervention device is a delivery system.

According to a thirteenth embodiment of the method, there is provided a method according to one of the first to eleventh embodiments, wherein the intervention device is a catheter.

Of course, although the present description discusses the placement of devices for deployment in cerebral endovascular regions, the technique described herein is also applicable to any situation where the deployment of a device for deployment inside an object, such as a patient, must be determined in real-time according to the localization of the intervention device used to deploy the device for deployment.

In another exemplary embodiment of the present invention, a computer program or a computer program element is provided that is characterized by being adapted to execute the method steps of the method according to one of the preceding embodiments, on an appropriate system.

In addition, a computer readable medium having stored the program element described previously is provided.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing device for medical device deployment prediction, comprising:
   an input unit;
   a processing unit; and
   an output unit;
   wherein the input unit is configured to provide to the processing unit 3D object data of a region of interest of an object; and 3D device model data of a device for deployment inside the object using an intervention device; and live intervention image data of the region of interest comprising spatial information of an intervention device provided for the deployment of the device for deployment;
   wherein the processing unit is configured to localize the intervention device within the 3D object data based exclusively on a detection of the intervention device in the live intervention image data, and then to perform a spatial registration of the intervention image data and the 3D object data;
   wherein the processing unit is configured to adapt the 3D device model data according to the 3D object data of the region of interest using the localization of the intervention device within the 3D object data, and to embed the adapted 3D device model data, representing the device for deployment, within the 3D data of the region of interest; thus generating an expected spatial relationship between the device for deployment and the region of interest of the object; and
   wherein the output unit is configured to display the expected spatial relationship.

2. The image processing device according to claim 1,
   wherein the input unit is further configured to receive a display command from a user;
   wherein the processing unit is further configured to generate the expected spatial relationship upon reception of the display command.

3. The image processing device according to claim 1,
   wherein the processing unit is further configured to monitor the live intervention image data of the intervention device, and to generate the expected spatial relationship when a change of the speed of the device for deployment is below a trigger threshold.

4. The image processing device according to claim 1,
   wherein the processing unit is configured to monitor the live intervention image data of the intervention device; and to generate the expected spatial relationship when a change of the deployment angle of the device for deployment in the live intervention image data exceeds a trigger threshold.

5. The image processing device according to claim 1, wherein the input unit is configured to provide final optimal deployment position data of the device for deployment to the processing unit;
wherein the processing unit is further configured to calculate i) a difference metric between the final optimal deployment position data of the device for deployment, and the adapted 3D device model data according to the 3D object data of the region of interest, using the localization of the intervention device within the 3D object data; and wherein the processor is further configured to calculate ii) a difference metric between final optimal deployment position data of the device for deployment and the adapted 3D device model data; and
wherein the output unit is configured to display the difference metric between a final optimal deployment position of the device for deployment and the adapted 3D device model data.

6. The image processing device according to claim 5, wherein the output unit is configured to display a representation of a first device for deployment in the final optimal deployment position of the device for deployment in the 3D object data of a region of interest, and to display a representation of a second device for deployment in a position defined by the localization, in the 3D object data of a region of interest, wherein the position of the second device for deployment is displayed according to the expected spatial relationship between the second device for deployment and the region of interest of the object.

7. The image processing device according to claim 1, wherein the processing unit is configured to use the live intervention image data to calculate the localization data, wherein the localization data is selected from the group of:
i) the instantaneous position of the intervention device relative to the region of interest;
ii) the instantaneous orientation of the intervention device relative to the region of interest;
iii) a prior trajectory of the intervention device; or
iv) any combination of i) to iii).

8. The image processing device according to claim 1, wherein the live intervention image data of the localization of the intervention device is from an electromagnetic localizer.

9. The image processing device according to claim 1, wherein the device for deployment is selected from the group of: flow diverters, stents, coils, or a woven endobridge.

10. The image processing device according to claim 9, wherein the intervention device is a delivery system.

11. The image processing device according to claim 9, wherein the intervention device is a catheter.

12. A medical imaging system, for medical device deployment prediction comprising:
an image acquisition arrangement;
a device according to claim 11; and
a display unit;
wherein the image acquisition arrangement is adapted to acquire the image data and to provide the data to the processing unit.

13. A method for operating an image processing device for medical device deployment prediction, comprising the steps of:
a) providing 3D object data of a region of interest of an object;
b) providing 3D device model data of a device for deployment inside the object using an intervention device;
c) providing live intervention image data of the region of interest comprising spatial information of an intervention device provided for the deployment of the device for deployment;
d) localizing the intervention device within the 3D object data based exclusively on a detection of the intervention device in the live intervention image data, and then performing a spatial registration of the intervention image data and the 3D object data;
e) adapting the 3D device model data according to the 3D object data of the region of interest using the localization of the intervention device within the 3D object data; and embedding the adapted 3D device model data, representing the device for deployment, within the 3D data of the region of interest; thus generating an expected spatial relationship between the device for deployment and the region of interest of the object; and
f) displaying the expected spatial relationship.

14. A non-transitory computer readable medium storing software configured to control a processing unit to perform the method according to claim 13.

15. An image processing device for medical device deployment prediction, comprising:
an input configured to provide a 3D image of a region of interest of a patient, a 3D model of an interventional device for deployment inside the region of interest, and a live image of the region of interest including spatial information regarding a position of the interventional device for the deployment of the interventional device;
one or more processors configured to:
localize the intervention device within the 3D image of the region of interest based exclusively on detection of the interventional device in the live image of the region of interest,
spatially register the live image of the region of interest and the 3D image of the region of interest,
adapt the 3D model of the interventional device according to the 3D image of the region of interest using the localization of the interventional device within the 3D image of the region of interest,
embed the adapted 3D model of the interventional device within the 3D image of the region of interest, thereby generating an expected spatial relationship between the interventional device and the region of interest of the patient; and
a display device configured to display the expected spatial relationship.

* * * * *